|                          |              |
| ------------------------ | ------------ |
| United States Patent [19] | [11] 4,061,616 |
| Murayama et al.          | [45] Dec. 6, 1977 |

[54] STABILIZATION OF SYNTHETIC POLYMERS

[75] Inventors: Keisuke Murayama; Syoji Morimura; Takao Yoshioka; Tomoyuki Kurumada, all of Tokyo, Japan

[73] Assignee: Sankyo Company Limited, Tokyo, Japan

[21] Appl. No.: 610,334

[22] Filed: Sept. 4, 1975

Related U.S. Application Data

[63] Continuation of Ser. No. 472,370, May 22, 1974, abandoned.

[30] Foreign Application Priority Data

June 15, 1973   Japan .................................. 48-68144

[51] Int. Cl.$^2$ ............................................... C08K 5/34
[52] U.S. Cl. .............................. 260/45.8 N; 260/75 N; 260/77.5 SS; 260/293.63
[58] Field of Search ................................... 260/45.8 N

[56] References Cited

U.S. PATENT DOCUMENTS

| 2,778,825 | 1/1957  | Melamed .............................. 260/244 |
| 3,072,667 | 1/1963  | Meltzer et al. ...................... 260/294.7 |
| 3,640,928 | 2/1972  | Murayama et al. .................... 260/23 |
| 3,759,926 | 9/1973  | Chalmers et al. ................. 260/293.9 |
| 3,847,930 | 11/1974 | Randell et al. ........................ 260/297 |
| 3,853,890 | 12/1974 | Holt ................................. 260/293.63 |
| 4,014,887 | 3/1977  | Randell et al. .................. 260/293.84 |

*Primary Examiner*—Donald E. Czaja
*Assistant Examiner*—R. A. White
*Attorney, Agent, or Firm*—Toren, McGeady and Stanger

[57] ABSTRACT

A synthetic polymer composition stabilized against photo- and thermal deterioration thereof wherein there is incorporated, in a sufficient amount to prevent such deterioration, bipiperidyl derivatives.

8 Claims, No Drawings

STABILIZATION OF SYNTHETIC POLYMERS

CROSS-REFERENCES TO RELATED APPLICATIONS

This application is a Continuation of copending application Ser. No. 472,370, filed May 22, 1974, now abandoned.

This invention relates to a synthetic polymer composition. More particularly, it is concerned with a synthetic polymer composition stabilized against photo- and thermal deterioration thereof wherein there is incorporated a bipiperidyl derivative in a sufficient amount to prevent such deterioration.

Several 4,4'-dihydroxy-4,4'-bipiperidyl derivatives are known in J. Org. Chem., 27, 1695 (1962) as to their utility for pharmaceuticals. However, their utility for stabilizer for synthetic polymers has not been known yet. Now, the inventors have found that bipiperidyl derivatives having the following formula (I) or an acid addition salt thereof show remarkable stabilizing effect for synthetic polymers against photo- and thermal degradation thereof

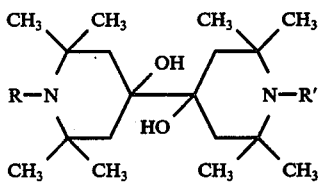

wherein R and R', which may be the same or different, and each represents hydrogen atom, an alkyl group, an alkenyl group, an alkynyl group, an aralkyl group, a hydroxyalkyl group, an alkoxyalkyl group, an aliphatic or aromatic acyloxyalkyl group, a cyanoalkyl group, a halogenoalkyl group, an epoxyalkyl group, an alkoxycarbonylalkyl group, an aliphatic acyl group, an alkoxycarbonyl group or an aralkoxycarbonyl group.

By dint of excellent characteristic properties, synthetic polymers are broadly used in various forms such as fibers, films, sheets, other shaped articles, latexes and foams. However, these polymeric materials are defective in that the stability to light and heat is poor. Various stabilizers are known as agents for preventing deterioration of these synthetic polymers. However, these known stabilizers still involve problems to be solved.

It is a primary object of this invention to provide a stabilizer for synthetic polymers which comprises a bipiperidyl derivative of the above formula (I) or an acid addition salt thereof. Another object of the invention is to provide a synthetic polymer composition stabilized to deterioration, which comprises a synthetic polymer and, incorporated therein, at least one of bipiperidyl derivatives of the formula (I) or an acid addition salt thereof in an amount sufficient to prevent deterioration.

In the above general formula (I), as R and R', there can be mentioned; hydrogen atom; alkyl groups having 1 to 8, preferably 1 to 4 carbon atoms such, for example as methyl, ethyl, propyl, butyl and octyl groups; alkenyl groups having 3 to 6 carbon atoms such, for example, as allyl, crotyl and 2-hexenyl, preferably allyl group; alkynyl groups having 3 or 4 carbon atoms preferably 2-propynyl group; aralkyl groups having 6 carbon atoms in the aryl and 1 or 2 carbon atoms in the alkyl such, for example, as benzyl and phenethyl groups; hydroxyalkyl groups having 1 to 4 carbon atoms, preferably 2-hydroxyethyl group; alkoxyalkyl groups having 1 to 8, preferably 1 to 4 carbon atoms in the alkoxy and 1 to 4, preferably 1 or 2 carbon atoms in the alkyl, such, for example, as 2-ethoxyethyl, ethoxymethyl, 2-propoxyethyl and 3-methoxypropyl groups; aliphatic acyloxyalkyl groups of which acyl is either saturated and having 2 to 18 carbon atoms or unsaturated and having 3 to 6 carbon atoms, and of which alkyl having 1 to 4, preferably 2 carbon atoms such, for example, as 2-acetoxyethyl, 2-stearoyloxyethyl, 2-acryloyloxyethyl, 2-methacryloyloxyethyl, 2-crotonoyloxyethyl and 2-sorboyloxyethyl groups; aromatic acyloxyalkyl groups of which aromatic ring may be substituted with 1 to 3 substituents selected from an alkyl having 1 to 4 carbon atoms and hydroxy, and of which alkyl having 1 to 4, preferably 2 carbon atoms, preferably substituted or unsubstituted benzoyloxyalkyl groups such, for example, as 2-benzoyloxyethyl, 2-(p-tert.-butylbenzoyloxy)ethyl and 2-salicyloyloxyethyl groups; cyanoalkyl groups having 2 or 3 carbon atoms such, for example, as 2-cyanoethyl and cyanomethyl groups; halogenoalkyl groups having 1 to 3 carbon atoms such, for example, as 2-chloroethyl group; epoxyalkyl groups, preferably 2,3-epoxypropyl group; alkoxycarbonylalkyl groups having 1 to 18, preferably 1 to 8 carbon atoms in the alkoxy and 1 or 2 carbon atoms in the alkyl such, for example, as ethoxycarbonylmethyl, butoxycarbonylmethyl, hexyloxycarbonylmethyl and octyloxycarbonylmethyl groups, aliphatic acyl groups which may be saturated and having 2 to 8 carbon atoms or, preferably, unsaturated and having 3 or 4 carbon atoms such, for example, as acetyl, propionyl, butyryl, acryloyl, and methacryloyl groups; alkoxycarbonyl groups having 2 to 9 carbon atoms such, for example, as methoxycarbonyl, butoxycarbonyl and octyloxycarbonyl groups; and aralkoxycarbonyl groups, preferably benzyloxycarbonyl group.

As the acid component of the acid addition salts, there can be mentioned, for instance, organic acids such as benzoic acid, p-tert.-butylbenzoic acid, 3,5-di-tert.-butyl-4-hydroxyphenylpropionic acid maleic acid, oxalic acid, acetic acid, methylsulfonic acid and p-toluenesulfonic acid, and inorganic acids such as sulfuric acid, phosphoric acid and hydrochloric acid.

In this invention it is preferred that both of R and R' represent hydrogen atom, an alkyl group having 1 to 4 carbon atoms, allyl group, benzyl group, an alkoxyalkyl group having 1 to 4 carbon atoms in the alkoxy and 1 or 2 carbon atoms in the alkyl, aliphatic acyloxyethyl groups of which acyl is either saturated and having 2 to 18 carbon atoms or unsaturated and having 3 to 6 carbon atoms, benzoyloxyethyl group of which benzene ring may be substituted with 1 to 3 substituents selected from an alkyl having 1 to 4 carbon atoms and hydroxy, or an alkoxycarbonylmethyl group having 1 to 8 carbon atoms in the alkoxy.

It is especially preferred that both of R and R' represent hydrogen atom, an alkyl group having 1 to 4 carbon atoms, allyl group, benzyl group or alkoxycarbonylmethyl group having 1 to 8 carbon atoms in the alkoxy.

As typical instance of the bipiperidyl derivative (I) of this invention, there can be mentioned the following compounds:

1. 4,4'-dihydroxy-2,2,6,6,2',2',6',6'-octamethyl-4,4'-bipiperidyl,
2. 4,4'-dihydroxy-1,2,2,6,6,1',2',2',6',6'-decamethyl-4,4'-bipiperidyl, 3. 4,4'-dihydroxy-2,2,6,6,2',2',6',6'-octamethyl-1,1'-dioctyl-4,4'-bipiperidyl,
4. 1,1'-diallyl-4,4'-dihydroxy-2,2,6,6,2',2',6',6'-octamethyl-4,4'-bipiperidyl,
5. 4,4'-dihydroxy-2,2,6,6,2',2',6',6'-octamethyl-1,1'-di(2-propynyl)-4,4'-bipiperidyl,
6. 1,1'-dibenzyl-4,4'-dihydroxy-2,2,6,6,2',2',6',6'-octamethyl-4,4'-bipiperidyl,
7. 4,4'-dihydroxy-1,1'-bis(2-hydroxyethyl)-2,2,6,6,2',2',6',6'-octamethyl-4,4'-bipiperidyl,
8. 1,1'-bis(2-ethoxyethyl)-4,4'-dihydroxy-2,2,6,6,2',2',6',6'-octamethyl-4,4'-bipiperidyl,
9. 1,1'-bis(2-acetoxyethyl)-4,4'-dihydroxy-2,2,6,6,2',2',6',6'-octamethyl-4,4'-bipiperidyl,
10. 4,4'-dihydroxy-2,2,6,6,2',2',6',6'-octamethyl-1,1'-bis(2-stearoyloxyethyl)-4,4'-bipiperidyl,
11. 1,1'-bis(2-acryloyloxyethyl)-4,4'-dihydroxy-2,2,6,6,2',2',6',6'-octamethyl-4,4'-bipiperidyl,
12. 4,4'-dihydroxy-1,1'-bis(2-methacryloyloxyethyl)-2,2,6,6,2',2',6',6'-octamethyl-4,4'-bipiperidyl,
13. 1,1'-bis(2-crotonoyloxyethyl)-4,4'-dihydroxy-2,2,6,6,2',2',6',6'-octamethyl-4,4'-bipiperidyl,
14. 4,4'-dihydroxy-2,2,6,6,2',2',6',6'-octamethyl-1,1'-bis(2-sorboyloxyethyl)-4,4'-bipiperidyl,
15. 1,1'-bis(2-benzoyloxyethyl)-4,4'-dihydroxy-2,2,6,6,2',2',6',6'-octamethyl-4,4'-bipiperidyl,
16. 1,1'-bis(2-p-tert-butylbenzoyloxyethyl)-4,4'-dihydroxy-2,2,6,6,2',2',6',6'-octamethyl-4,4'-bipiperidyl,
17. 4,4'-dihydroxy-2,2,6,6,2',2',6',6'-octamethyl-1,1'-bis(2-salicyloyloxyethyl)-4,4'-bipiperidyl
18. 1,1'-bis(cyanomethyl)-4,4'-dihydroxy-2,2,6,6,2',2',6',6'-octamethyl-4,4'-bipiperidyl,
19. 1,1'-bis(2-chloroethyl)-4,4'-dihydroxy-2,2,6,6,2',2',6',6'-octamethyl-4,4'-bipiperidyl,
20. 1,1'-bis(2,3-epoxypropyl)-4,4'-dihydroxy-2,2,6,6,2',2',6',6'-octamethyl-4,4'-bipiperidyl,
21. 1,1'-bis(ethoxycarbonylmethyl)-4,4'-dihydroxy-2,2,6,6,2',2',6',6'-octamethyl-4,4'-bipiperidyl,
22. 4,4'-dihydroxy-2,2,6,6,2',2',6',6'-octamethyl-1,1'-bis(octyloxycarbonylmethyl)-4,4'-bipiperidyl,
23. 1-acetyl-4,4'-dihydroxy-2,2,6,6,2',2',6',6'-octamethyl-4,4'-bipiperidyl,
24. 1,1'-diacetyl-4,4'-dihydroxy-2,2,6,6,2',2',6',6'-octamethyl-4,4'-bipiperidyl,
25. 1,1'-diacryloyl-4,4'-dihydroxy-2,2,6,6,2',2',6',6'-octamethyl-4,4'-bipiperidyl,
26. 1,1'-bis(butoxycarbonyl)-4,4'-dihydroxy-2,2,6,6,2',2',6',6'-octamethyl-4,4'-bipiperidyl, and
27. 1,1'-bis(benzyloxycarbonyl)-4,4'-dihydroxy-2,2,6,6,2',2',6',6'- octamethyk-4,4'- bipiperidyl.

Among bipiperidyl derivatives of the above formula (I) to be used in this invention, those in which each of R and R' represents hydrogen atom or methyl group are disclosed in the above-mentioned literature.

However, other compounds of this invention expressed by the formula (I) are novel compounds.

The bipiperidyl derivatives of this invention expressed by the above formula (I) can be synthesized according to methods expressed by the following reaction formulae:

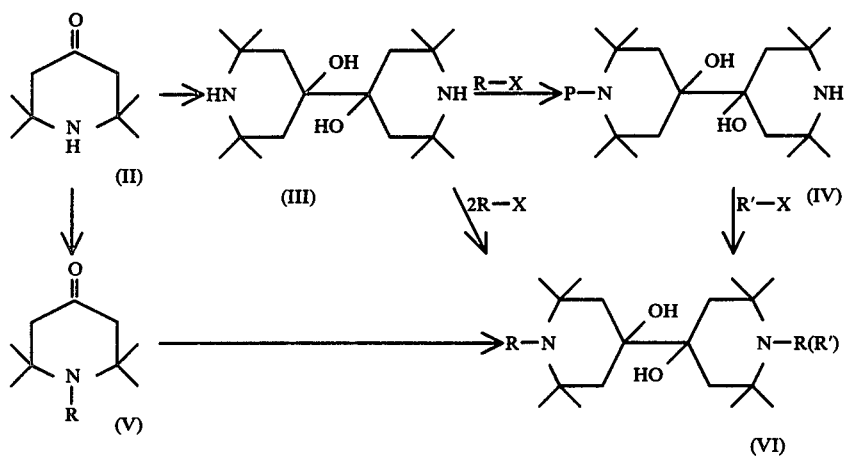

in which R and R' are as defined above, and X designates a halogen atom.

When compounds of the formula (III) are reacted with a halide (R-X) in the presence of an organic or inorganic base as an acid binding agent, compounds of the formula (IV) are obtained in the case of the equimolar reaction, but if the halide is used in an amount of two moles per mole of the compound of the formula (III), compounds of the formula (VI) are obtained. Similarly, compounds of the formula (VI) can be prepared from compounds of the formula (IV).

A compound of the formula (VI) in which both R and R' represent methyl group can also be obtained in a high yield by reacting the compound of the formula (III) with formic acid and formalin.

Further, a compound of the formula (VI) in which both R and R' represent a 2-hydroxyethyl group can be prepared by reacting the compound of the formula (III) with ethylene oxide in the presence of an acid.

Furthermore, it has been found that preparation of compounds of the formula (III) or (VI) from compounds of the formula (II) or (V) can be made more advantageously by the following method than by the conventional method described above. More specifically, the intended compound of the formula (III) or (VI) can be obtained in a yield exceeding 80% by reacting under heating metallic sodium and an acid with a compound of the formula (II) or (V) dissolved in a non-polar solvent.

In practicing the above-mentioned improved process, a compound of the formula (II) or (V) is dissolved in a non-polar solvent such as benzene, toluene and xylene and metallic sodium and an acid are added thereto to effect the reaction. It is desired that metallic sodium is employed in an amount of 2 to 3 moles per mole of the compound of the formula (II) or (V).

In the reaction of the improved process, the presence of an acid is particularly important for increasing the yield of the intended product. In general, in the absence of an acid synthesis of a pinacol compound from a ketone proceeds only with a low yield (see Bull. Soc. Chim. France, 1946, 256). The acid is preferably used in an amount of 1 to 1.2 moles per mols of metallic sodium used.

As the acid, there can be employed organic acids such as acetic acid, benzoic acid and p-toluenesulfonic acid, and inorganic acids such as hydrochloric acid gas.

The reaction temperature is not particularly critical, but it is desired that the reaction is carried out at a boiling point of a solvent used. In general, the reaction is accomplished by conducting heating at 50° to 100° C for 30 minutes to 5 hours.

After termination of the reaction, the intended product is collected according to customary procedures. For instance, the reaction mixture is filtered, the filtrate is concentrated, and the residual crystals are collected and, if necessary, purified by recrystallization.

In this invention, the term "synthetic polymer" as used herein are intended to embrace:
polyolefins including
  homopolymers of olefins such as low-density and high-density polyethylene, polypropylene, polystyrene, polybutadiene, polyisoprene, homopolymers of other olefins, and copolymers of olefins with other ethylenically unsaturated monomers such as ethylene-propylene, copolymer, ethylene-butene copolymer, ethylene-vinyl acetate copolymer, styrene-butadiene copolymer, acrylonitrile-styrene-butadiene copolymer and copolymers of other ethylene-forming unsaturated monomers with olefins;
polyvinyl chlorides and polyvinylidene chlorides
  including homopolymers of each of vinyl chloride and vinylidene chloride, vinyl chloride-vinylidene chloride copolymer and copolymers of each of vinyl chloride and vinylidene chloride with vinyl acetate or other ethylene-forming unsaturated monomers; polyacetal, such as polyoxymethylene and polyoxyethylene; polyesters such as polyethylene terephthalate; polyester ethers; polyamides such as 6-nylon, 6,6-nylon, 6,10-nylon and 10-nylon;
polyurethanes;
polycarbonates;
and epoxy resins.

The bipiperidyl derivative (I) to be used as a stabilizer in this invention can easily be incorporated in a synthetic polymer by various methods ordinarily adopted in the art. The stabilizer can be added to a synthetic polymer at an optional stage of the preparation of a shaped article. For instance, the stabilizer is mixed in the form of a dry powder with a synthetic polymer, or a suspension or emulsion of the stabilizer is mixed with a synthetic polymer.

The amount of the bipiperidyl derivative (I) to be added to a synthetic polymer according to this invention can be varied in a broad range depending on the kind and properties of the synthetic polymeric material and the particular use of the resulting composition to be stabilized. In general, it is added in an amount ranging from 0.01 to 5% by weight based on the amount of synthetic polymer, but a practical range differs depending on the kind of the synthetic polymer. For instance, in the case of a polyolefin, the stabilizer is added in an amount of 0.01 to 2.0% by weight, preferably 0.02 to 1.0% by weight, and in the case of a polyvinyl chloride or polyvinylidene chloride, the stabilizer is incorporated in an amount of 0.01 to 1.0% by weight, preferably 0.02 to 0.5% by weight. In the case of a polyurethane or polyamide, the stabilizer is added in an amount of 0.01 to 5.0% by weight, preferably 0.02 to 2.0% by weight.

The stabilizer of this invention can be used singly or in combination with known antioxidants, UV-absorbers, metal deactivators, fillers, organic pigments and other additives. Especially when the stabilizer of this invention is used in combination with a UV-absorber for an organic pigment-containing polymer, the reduction of the light stabilizing effect of the UV-absorber caused by the organic pigment is prevented and hence, particularly good results can be obtained.

Instances of antioxidants, UV-absorbers and other additives to be used in combination with the stabilizer of this invention will now be described.

Antioxidants 2,6-Dialkylphenols, such, for example, as 2,6-di-tert.-butyl-4-methylphenol, 2-tert.-butyl-4,6-dimethylphenol, 2,6-di-tert.-butyl-4-methoxymethylphenol and 2,6-dioctadecyl-4-methylphenol.

Derivatives of alkylated hydroquinones, such, for example, as 2,5-di-tert.-butyl-hydroquinone, 2,5-di-tert.-amyl-hydroquinone, 2,6-di-tert.-butyl-hydroquinone, 2,5-di-tert.-butyl-4-hydroxy-anisole, 3,5-di-tert.-butyl-4-hydroxy-anisole, tris(3,5-di-tert.-butyl-4-hydroxyphenyl)-phosphite, 3,5-di-tert.-butyl-4-hydroxyphenyl-stearate and di-(3,5-di-tert.-butyl-4-hydroxyphenyl)-adipate.

Hydroxylated thiodiphenyl ethers, such, for example, as 2,2'-thiobis(6-tert.-butyl-4-methylphenol), 2,2'-thiobis-(4-octylphenol), 4,4'-thiobis(6-tert.-butyl-3-methylphenol), 4,4'-thiobis(3,6-di-sec.-amylphenol) and 4,4'-thiobis(6-tert.-butyl-2-methylphenol), 4,4'-bis(2,6-dimethyl-4-hydroxyphenyl)-disulfide.

Alkylidene-bisphenols, such, for example, as 2,2'-methylene-bis(6-tert.-butyl-4-methylphenol), 2,2'-methylene-bis(6-tert.-butyl-4-ethylphenol), 4,4'-methylene-bis(6-tert.-butyl-2-methylphenol), 4,4'-methylene-bis(2,6-di-tert.-butylphenol), 2,6-bis(3-tert.-butyl-5-methyl-2-hydroxybenzyl)-4-methylphenol, 2,2'-methylene-bis[4-methyl-6-(α-methylcyclohexyl)phenol], 1,1-bis(3,5-dimethyl-2-hydroxyphenyl)-butane, 1,1-bis(5-tert.-butyl-4-hydroxy-2-methylphenyl)-butane, 2,2-bis(5-tert.-butyl-4-hydroxy-2-methylphenyl)-butane, 2,2-bis(3,5-di-tert.-butyl-4-hydroxyphenyl)-propane, 1,1,3-tris(5-tert.-butyl-4-hydroxy-2-methylphenyl)butane, 2,2-bis(5-tert.-butyl-4-hydroxy-2-methylphenyl-4-n-dodecylmercaptobutane, 1,1,5,5-tetra-(5-tert.-butyl-4-hydroxy-2-methylphenyl)-pentane and ethylene glycol bis[3,3-bis(3'-tert.-butyl-4'-hydroxyphenyl)-butyrate].

O-, N- and S-benzyl compounds, such, for example, as 3,5,3',5'-tetra-tert.-butyl-4,4'-dihydroxydibenzylether, 4-hydroxy-3,5-dimethylbenzyl-mercaptoacetic acid octadecyl ester, tri-(3,5-di-tert.-butyl-4-hydroxybenzyl)-amine, and bis-(4-tert.-butyl-3-hydroxy-2,6-dimethylbenzyl)-dithiol terephthalate.

Hydroxybenzylated malonic esters, such, for example, as 2,2-bis(3,5-di-tert.-butyl-2-hydroxybenzyl)-malonic acid dioctadecyl ester, 2-(3-tert.-butyl-4-hydroxy-5-methylbenzyl)-malonic acid dioctadecyl ester, 2,2-bis(3,5-di-tert.-butyl-4-hydroxybenzyl)-malonic acid di-dodecylmercaptoethyl ester and 2,2-bis(3,5-di-tert.-butyl-4-hydroxybenzyl)-malonic acid di-(4-tert.-octylphenyl) ester.

Hydroxybenzyl-aromatics, such, for example, as 1,3,5-tri-(3,5-di-tert.-butyl-4-hydroxybenzyl)-3,4,6-trimethylbenzene, 1,4-di-(3,5-di-tert.-butyl-4-hydroxybenzyl)-2,3,5,6-tetramethylbenzene and 2,4,6-tri-(3,5-di-tert.-butyl-4-hydroxybenzyl)-phenol.

s-Triazine compounds, such, for example, as 2,4-bis-octylmercapto-6-(3,5-di-tert.-butyl-4-hydroxyanilino)-s-triazine, 2-octylmercapto-4,6-bis(3,5-di-tert.-butyl-4-hydroxyanilino)-s-triazine, 2-octylmercapto-4,6-bis(3,5-di-tert.-butyl-4-hydroxyphenoxy)-s-triazine, 2,4,6-tris(3,5-di-tert.-butyl-4-hydroxyphenoxy)-s-triazine, 2,4,6,-tris(3,5-di-tert.-butyl-4-hydroxyphenylethyl)-s-triazine and 1,3,5-tris(3,5-di-tert.-butyl-4-hydroxybenzyl)-isocyanurate.

Amides of 3,5-di-tert.-butyl-4-hydroxyphenyl-propionic acid, such, for example, as 1,3,5-tri-(3,5-di-tert.-butyl-4-hydroxyphenyl-propionyl)-hexahydro-s-triazine and N,N'-di-(3,5-di-tert.-butyl-4-hydroxyphenyl-propionyl)-hexamethylenediamine.

Esters of 3,5-di-tert.-butyl-4-hydroxyphenyl-propionic acid with monohydric or polyhydric alcohols, such, for example, as methanol, ethanol, octadecanol, 1,6-hexanediol; 1,9-nonanediol, ethylene glycol, 1,2-propane-diol, diethylene glycol, thiodiethylene glycol, neopentyl glycol, pentaerythritol, 3-thia-undecanol, 3-thiapentadecanol, trimethylhexanediol, trimethylolethane, trimethylolpropane, tris-hydroxyethyl-iso-cyanurate and 4-hydroxymethyl-1-phospha-2,6,7-trioxabicyclo[2,2,2]-octane.

Esters of 5-tert.-butyl-4-hydroxy-3-methylphenylproponic acid with monohydric or polyhydric alcohols, such, for example, as methanol, ethanol, octadecanol, 1,6-hexanediol, 1,9-nonanediol, ethylene glycol, 1,2-propanediol, diethylene glycol, thiodiethylene glycol, neopentyl glycol, pentaerythritol, 3-thia-undecanol, 3-thia-pentadecanol, trimethylhexanediol, trimethylolethane, trimethylolpropane, tris-hydroxyethyl-isocyanurate and 4-hydroxymethyl-1-phospha-2,6,7-trioxabicyclo[2,2,2]octane.

Esters of 3,5-di-tert.-butyl-4-hydroxyphenylacetic acid with monohydric or polyhydric alcohols, such, for example, as methanol, ethanol, octadecanol, 1,6-hexanediol, 1,9-nonanediol, ethylene glycol, 1,2-propanediol, diethylene glycol, thiodiethylene glycol, neopentyl glycol, pentaerythritol, 3-thia-undecanol, 3-thiapentadecanol, trimethylhexanediol, trimethylolethane, trimethylolpropane, tris-hydroxyethyl-isocyanurate and 4-hydroxymethyl-1-phospha-2,6,7-trioxabicyclo[2,2,2,]-octane.

Acylaminophenols, such, for example, as N-(3,5-di-tert.-butyl-4-hydroxyphenyl)-stearic acid amide and N,N-di-(3,5-di-tert.-butyl-4-hydroxyphenyl)-thio-bis-acetamide.

Benzylphosphonates, such, for example, as 3,5-di-tert.-butyl-4-hydroxybenzyl-phosphonic acid dimethyl ester, 3,5-di-tert.-butyl-4-hydroxybenzyl-phosphonic acid diethyl ester, 3,5-di-tert.-butyl-4-hydroxybenzyl-phosphonic acid dioctadecyl ester and 5-tert.-butyl-4-hydroxy-3-methylbenzyl-phosphonic acid dioctadecyl ester.

Aminoaryl derivatives, such, for example, as phenyl-1-naphthylamine, phenyl-2-naphthylamine, N,N'-diphenyl-p-phenylenediamine, N,N'-di-2-naphthyl-p-phenylene-diamine, N,N'-di-sec.-butyl-p-phenylenediamine, 6-ethoxy-2,2,4-trimethyl-1,2-dihydroquinoline, 6-dodecyl-2,2,4-trimethyl-1,2-dihydroquionoline, mono- and dioctylimino-dibenzyl and polymerised 2,2,4-trimethyl-1,2-dihydroquinoline.

UV-Absorbers and light protection agents.

2-(2'-Hydroxyphenyl)-benztriazoles, such, for example, as the 5'-methyl-,3',5'-di-tert.-butyl-,5'-tert.-butyl-, 5'-(1,1,3,3-tetramethyl-butyl)-, 5-chloro-3',5'-ditert.-butyl-, 5-chloro-3'-tert.-butyl-5'-methyl-, 3'-sec.-butyl-5'-tert.-butyl-, 3'-(α-methyl-benzyl)-5'-methyl-, 3')-α-methylbenzyl)-5'-methyl-5-chloro-,4'-hydroxy-, 4'-methoxy-,4'-octoxy-, 3', 5'-di-tert.-amyl-, 3'-methyl-5'-carbomethoxyethyl- and 5-chloro-3',5'-di-tert.-amyl-derivatives.

2,4-Bis-(2'-hydroxyphenyl)-6-alkyl-s-triazines, such, for example, as the 6-ethyl-, 6-undecyl- and 6-heptadecyl-derivatives.

2-Hydroxy-benzophenones, such, for example, as the 4-hydroxy-, 4-methoxy-, 4-octoxy-, 4-decyloxy-, 4-dodecyloxy-, 4-benzyloxy-, 4,2',4'-trihydroxy- and 2'-hydroxy-4,4'-dimethoxy-derivatives.

1,3-Bis-(2'-hydroxy-benzoyl)-benzenes, such, for example, as 1,3-bis-(2'-hydroxy-4'-hexyloxy-benzoyl)-benzene, 1,3-bis-(2'-hydroxy-4'-octoxy-benzoly)-benzene and 1,3--bis-(2'-hydroxy-4'-dodecyloxy-benzoyl)-benzene.

Esters of optionally substituted benzoic acids, such, for example, as phenyl salicylate, octylphenyl salicylate, di-benzoylresorcinol, bis-(4-tert.-butyl-benzoyl)-resorcinol, benzoyl-resorcinol, 3,5-di-tert.-butyl-4-hydroxybenzoic acid 2,4-di-tert.-butyl-phenyl ester, octadecyl ester or 2-methyl-4,6-di-tert.-butylphenyl ester.

Acrylates, such, for example, as α-cyano-β, β-diphenylacrylic acid ethyl ester or isooctyl ester, α-carbomethoxy-cinnamic acid methyl ester, α-cyano-β-methyl-p-methoxy-cinnamic acid methyl ester or butyl ester and N-(β-carbomethoxyvinyl)-2-methylindoline.

Nickel compounds, such, for example, as nickel complexes of 2,2'-thio-bis-(4-tert.-octylphenol), such as the 1:1 and 1:2 complex, optionally with other ligands such as n-butylamine, triethanolamine or N-cyclohexyl-diethanolamine; nickel complexes of bis(4-tert.-octylphenyl)-sulphone, such as the 2:1 complex, optionally with other ligands such as 2-ethyl-caproic acid, nickel dibutyl-dithiocarbamate, nickel salts of 4-hydroxy 3,5-di-tert.-butylbenzylphosphonic acid monoalkyl esters, such as the methyl, or butyl ester, the nickel complex of 2-hydroxy-4-methyl-phenyl-undecylketonoxime and nickel 3,5-di-tert.-butyl-4-hydroxybenzoate.

Oxalic acid diamides, such, for example, as 4,4'-dioctyloxyoxanilide, 2,2'-dioctyloxy-5,5'-di-tert.-butyloxanilide, 2,2'-di-dodecyloxy-5,5'-di-tert.-butyloxanilide, 2-ethoxy-5-tert.-butyl-2'-ethyl-oxanilide, 2-ethoxy-2'-ethyl-oxanilide, N,N'-bis-(3-dimethylaminopropyl) oxalamide, mixtures of o- and p-methoxy and o-and p-ethoxy-di-substitutec oxanilides and mixtures of 2-ethoxy-5-tert.-butyl-2'-ethyl-oxanilide with 2-ethoxy-2'-ethyl-5,4'-di-tert.-butyl-oxanilide.

Metal deactivators, such, for example, as oxanilide, isophthalic acid dihydrazide, sebacic acid bis-phenylhydrazide, bis-benzylidene oxalic acid dihydrazide, N,N'-diacetyl-adipic acid dihydrazide, N,N'-bis-salicycloyloxalic acid dihydrazide, N,N'-bis-salicyloyl-hydrazine and N,N'-bis(3,5-di-tert.-butyl-4-hydroxyphenyl-propionyl)-hydrazine.

Phosphites, such, for example, as triphenylphosphite, diphenyl alkyl-phosphites, phenyl dialkylphosphites, trinonylphenyl-phosphite, trilaurylphosphite, trioctadecylphosphite, 3,9-di-isodecyloxy-2,4,8,10-tetraoxa-3,9-diphospha-spiro[5,5]undecane and tri-(4-hydroxy-3,5-di-tert.-butylphenyl)-phosphite.

Compounds which destroy peroxides, such, for example, as esters of α-thiodipropionic acid, e.g. the lauryl, stearyl, myrystyl or tridecyl ester, salts of 2-mercaptobenzimidazole, e.g. the zinc salt, and diphenylthiourea.

Polyamide stabilizers, such, for example, as copper salts in combination with iodides and/or phosphorus compounds and salts of divalent manganese.

Basic co-stabilizers, such, for example, as polyvinylpyrrolidone, melamine, benzoguanamine, triallyl cyanurate, dicyandiamide, urea derivatives, hydrazine derivatives, amines, polyamides, poyurethanes and alkali metal salts and alkaline earth metal salts of higher saturated or unsaturated fatty acids, e.g. Ca stearate, Mg laurate, Na ricinoleate, K palmitate and Zn sterate.

PVC stabilizers, such, for example, as organic tin compounds, organic lead compounds and Ba/Cd salts of fatty acids.

Nucleating agents, such, for example, as 4-tert.-butylbenzoic acid, adipic acid and diphenylacetic acid.

Other additives, such, for example, as plasticizers, lubricants, e.g. glycerine monostearate, emulsifiers, antistatic agents, flameproofing agents, pigments, carbon black, asbestos, glass fibers, kaolin and talc.

The following examples are given solely for the purpose of illustrating the present invention.

In Examples 1 to 6 given hereinafter, compositions comprising a synthetic polymer and, incorporated therein, a bipiperidyl derivative (I) of this invention, and the stabilizing effect attained by such bipiperidyl derivative will be illustrated. In Examples 7 and 8, methods for preparation of bipiperidyl derivatives (I) will be illustrated.

EXAMPLE 1

0.25 part by weight of a stabilizer of this invention was melt-mixed with 100 parts by weight of a polypropylene ("Noblen JHH-G", trade name, available from Mitsui Toatsu Chemicals Inc.; recrystallized twice from monochlorobenzene), and the mixture was molded under pressure into a sheet having a thickness of 0.5 mm. The sheets thus prepared were exposed to ultraviolet ray in a Fade Meter at 45° C, and the times to embrittle were measured.

The results as shown in Table 1.

EXAMPLE 2

0.25 part by weight of a stabilizer of this invention was melt-mixed with 100 parts by weight of a high density polyethylene ("Hi-zex", trade name, available from Mitsui Toatsu Chemicals Inc.; recrystallized twice from toluene), and the mixture was molded under pressure into a sheet having a thickness of 0.5 mm. The sheets thus prepared were exposed to ultraviolet ray in a Fade Meter at 45° C, and the times to embrittle were measured.

The results are shown in Table 1.

Table 1

| Stabilizer Compound No. | Polypropylene | High Density Polyethylene |
|---|---|---|
| 1 | 900 hours | 2060 hours |
| 2 | 840 | 1900 |
| 4 | 1120 | 2380 |
| 6 | 940 | 2080 |
| 8 | 700 | 1340 |
| 21 | 780 | 1820 |
| none | 60 | 400 |

EXAMPLE 3

0.25 part by weight of a stabilizer of this invention was added to 100 parts by weight of a polystyrene ("Styron", trade name, available from Asahi Dow Limited; recrystallized from benzene-methanol), and the mixture was molded under pressure at 180° C into a plate having a thickness of 1.5 mm. This plate was irradiated in a xenon Fade-Meter (1.5 KW; Model FX-1 manufactured by Toyo Rika) for 3000 hours. The change of yellowness index of the so treated test piece was determined with use of a color-difference meter by Japanese Industrial Standard-K 7103. The change of yellowness index was calculated from the following equation:

$$\Delta YI = YI - YIo$$

wherein $\Delta YI$ means the change of yellowness index, YI means the yellowness index after exposure, and YIo means the initial yellowness index of the test piece.

The results are shown in Table 2.

Table 2

| Stabilizer Compound No. | YIo | $\Delta YI$ |
|---|---|---|
| 1 | 1.8 | 8.0 |
| 2 | 1.9 | 8.6 |
| 4 | 2.0 | 8.2 |
| 6 | 1.8 | 7.8 |
| none | 1.8 | 35.2 |

EXAMPLE 4

0.25 part by weight of a stabilizer of this invention was added to 100 parts by weight of a 6-nylon resin ("CM 1011", trade name, available from Toray Industries Inc.), and the blend was melt-mixed. The molten mixture was molded under pressure into a film having a thickness of about 0.1 mm by a molding press.

The resulting film was subjected to the accelerated aging test under the following conditions, and then, the tensile test was conducted to determine the elongation retention ratio and the tensile strength retention ratio.

1. Exposure to ultraviolet ray in a Fade Meter at 45° C for 200 hours.
2. Aging in a forced air oven at 160° C for 2 hours.

The results are shown in Table 3.

Table 3

| Stabilizer Compound No. | Fade-Meter | | Air oven | |
|---|---|---|---|---|
| | Elongation Retention ratio (%) | Tensile Strength Retention Ratio (%) | Elongation Retention Ratio (%) | Tensile Strength Retention Ratio (%) |
| 2 | 66 | 70 | 63 | 69 |
| 6 | 72 | 75 | 69 | 73 |
| none | 20 | 53 | 18 | 55 |

EXAMPLE 5

0.5 part by weight of a stabilizer of this invention was added to 100 parts by weight of polycaprolactone-type polyurethane ("Elastollan E-5080", trade name, available from Nippon Elastollan Industries Ltd.), and the mixture was heated, molten and then molded into a sheet having a thickness of about 0.5 mm.

The sheets thus prepared were exposed to ultraviolet ray in a Fade Meter at 45° C and the times to embrittle were measured and then it was subjected to the tensile test to determine the elongation retention ratio and the tensile strength retention ratio. The results are shown in Table 4.

Table 4

| Stabilizer Compound No. | Elongation Retention Ratio (%) | Tensile Strength Retention Ratio (%) |
| --- | --- | --- |
| 4 | 87 | 89 |
| 8 | 80 | 77 |
| 21 | 83 | 85 |
| none | 72 | 53 |

EXAMPLE 6

100 parts by weight of a polyester resin ("Ester-G13", trade name, available from Mitsui Toatsu Chemicals, Inc.) was incorporated with 1 part by weight of benzoyl peroxide and 0.2 part by weight of a stabilizer of this invention, and the mixture was stirred and dissolved throughly. The mixture was pre-heated at 60° C for 30 minutes and cured by heating it at 100° C for 1 hour to obtain a plate having a thickness of 3 mm. This plate was irradiated for 60 hours in a Sunshine Weather-Meter, and the change of yellowness index thereof was determined in the same manner as Example 3. The results are shown in Table 5.

Table 5

| Stabilizer Compound No. | YIo | ΔYI |
| --- | --- | --- |
| 1 | 2.6 | +8.4 |
| 4 | 2.4 | +8.1 |
| 6 | 2.2 | +8.7 |
| none | 1.9 | +13.3 |

EXAMPLE 7

31 g. of triacetoneamine was dissolved in 300 ml of toluene, and 18 g of acetic acid was added to the solution. The mixture was heated at 90°–105° C under agitation.

7 g. of metallic sodium in the form of small pieces was added little by little to the above solution. After the metallic sodium was dissolved completely, the reaction mixture was cooled and precipitated crystals were separated by filtration. The filtrate was concentrated and the residual crystals were recrystallized from benzene to obtain 27.4 g of intended 4,4'-dihydroxy-2,2,6,6,2',6',6'-octamethyl-4,4'-bipiperidyl in the form of white crystals melting at 177 to 178° C. The yield was 87.7%.

Results of the analysis of the product as $C_{18}H_{36}N_2O_2$ are as follows:

Calculated: C=69.18%, H=11.61%, N=8.77% Found: C=69.05%, H=11.53%, N=8.73% IR spectrum (Nujol mull): νOH 3500 cm$^{-1}$ and 3370 cm$^-$; νNH 3280 cm$^{-1}$ and 3240 cm$^{-1}$.

EXAMPLE 8

3.1 g of 4,4'-dihydroxy-2,2,6,6,2'2',6',6'-octamethyl-4,4'-bipiperidyl obtained in Example 7, 3.6 g. of allyl bromide, 4.5 g. of potassium hydrogencarbonate and 0.5 g. of p-toluenesulfonic acid were added to 30 ml. of dimethylformamide, and the mixture was heated at 120°–130° C for 5 hours under stirring.

The resulting reaction mixture was concentrated, and the residue was dissolved in benzene, washed with 5% aqueous sodium hydrogencarbonate solution and with water, dried over anhydrous potassium carbonate, and concentrated. Residual crystals were recrystallized from benzene to obtain the intended 1,1'-diallyl-4,4'-dihydroxy-2,2,6,6,2',2'6',6'-octamethyl-4,4'-bipiperidyl in the form of white crystals melting at 127 – 128° C.

Results of the analysis of the product as $C_{24}H_{44}N_2O_2$ are as follows: Calculated: C=73.42%, H=11.30%, N=7.14% Found: C=73.33%, H=11.24%, N=7.21% IR spectrum (Nujol mull):νOH 3220 cm$^{-1}$; νC=C 1640 cm$^{-1}$.

The following compounds were obtained according to the substantially same method described in Example 8:

4,4'-dihydroxy-1,2,2,6,6,1',2',2',6'6'-decamethyl-4,4'-bipiperidyl mp 148 ° ° – 149° C 1,1'-dibenzyl-4,4'-dihydroxy-2,2,6,6,2',2',6',6'-octamethyl-4,4'-bipiperidyl mp 216° – 217° C 4,4'-dihydroxy-1,1'-bis(2-hydroxyethyl)-2,2,6,6,2',2'6'6'-octamethyl-4,4'-bipiperidyl mp 286 – 288° C 1,1'-bis(2-ethoxyethyl)-4,4'-dihydroxy-2,2,6,6,2',2',6',6'-octamethyl-4,4'-bipiperidyl mp 167° – 169° C 1,1'-bis(2-acetoxyethyl)-4,4'-dihydroxy-2,2,6,6,2'2',6'6'-octamethyl-4,4'-bipiperidyl mp 206 ° – 207.5° C 1,1'-bis(2-crotonoyloxyethyl)-4,4'-dihydroxy-2,2,6,6,2',2',6',6'-octamethyl-4,4'-bipiperidyl mp 146.5 ° – 148° C 4,4'-dihydroxy-1,1'-bis(2,3-epoxypropyl)-2,2,6,6,2',2',6',6'-octamethyl-4,4'-bipiperidyl mp 167 ° – 169° C 1-acetyl-4,4'-dihydroxy-2,2,6,6,2',2',6',6'-octamethyl-4,4'-bipiperidyl mp 139° – 140° C

What is claimed is:

1. A synthetic polymer composition stabilized against photo- and thermal deterioration wherein there is incorporated, in a sufficient amount to prevent said deterioration, a compound having the formula

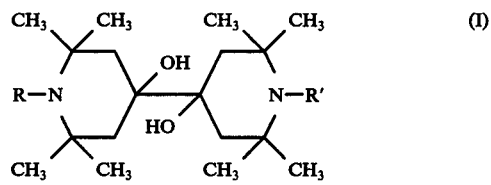

(I)

wherein R and R', which may be the same or different, and each represents hydrogen atom, an alkyl group, an alkenyl group, an alkynyl group, an aralkyl group, a hydroxyalkyl group, an alkoxyalkyl group, an aliphatic or aromatic acyloxyalkyl group, a cyanoalkyl group, a halogenoalkyl group, an epoxyalkyl group, an alkoxycarbonylalkyl group, an aliphatic acyl group, an alkoxycarbonyl group or an aralkoxycarbonyl group, or an acid addition salt thereof.

2. The synthetic polymer composition according to claim 1, wherein R and R', which may be the same or different, and each represents hydrogen atom, an alkyl group having 1 to 8 carbon atoms, an alkenyl group having 3 to 6 carbon atoms, an alkynyl group having 3 to 4 carbon atoms, an aralkyl group having 6 carbon atoms in the aryl and 1 or 2 carbon atoms in the alkyl, a hydroxyalkyl group having 1 to 4 carbon atoms, an alkoxyalkyl group having 1 to 8 carbon atoms in the alkoxy and 1 to 4 carbon atoms in the alkyl, an aliphatic acyloxyalkyl group of which acyl is either saturated and having 2 to 18 carbon atoms or unsaturated and having 3 to 6 carbon atoms, and of which alkyl having 1 to 4 carbon atoms, an aromatic acyloxyalkyl group of which aromatic ring may be substituted with 1 to 3 substituents selected from an alkyl having 1 to 4 carbon atoms and hydroxy, and of which alkyl having 1 to 4 carbon atoms, a cyanoalkyl group having 2 or 3 carbon atoms, a halogenoalkyl group having 1 to 3 carbon atoms, 2,3-epoxypropyl group, an alkoxycarbonylalkyl group having 1 to 18 carbon atoms in the alkoxy and 1 or 2 carbon atoms in the alkyl, an aliphatic acyl group which may be saturated and having 2 to 8 carbon atoms or unsaturated and having 3 or 4 carbon atoms, an alkoxycarbonyl group having 2 to 9 carbon atoms or an benzyloxycarbonyl group.

3. The synthetic polymer composition according to claim 1, wherein both of R and R' are hydrogen atom, an alkyl group having 1 to 4 carbon atoms, allyl group, benzyl group, an alkoxyalkyl group having 1 to 4 carbon atoms in the alkoxy and 1 or 2 carbon atoms in the alkyl, an aliphatic acyloxyethyl group of which acyl is either saturated annd having 2 to 18 carbon atoms or unsaturated and having 3 to 6 carbon atoms in the acyl, a benzoyloxyethyl group of which benzene ring may be substituted with 1 to 3 substituents selected from an alkyl having 1 to 4 carbon atoms and hydroxy or an alkoxycarbonylmethyl group having 1 to 8 carbon atoms in the alkoxy.

4. The synthetic polymer composition according to claim 1, wherein both of R and R' represent hydrogen atom, an alkyl group having 1 to 4 carbon atoms, allyl group, benzyl group or an alkoxycarbonylmethyl group having 1 to 8 carbon atoms in the alkoxy.

5. The synthetic polymer composition according to claim 1, wherein said compound (I) or an acid addition salt thereof is incorporated in an amount of 0.01 – 5.0% by weight, based on the amount of the synthetic polymer.

6. The synthetic polymer composition according to claim 1, wherein said polymer is a polyolefin.

7. The synthetic polymer composition according to claim 1, wherein said polymer is selected from a group consisting of a polyvinyl chloride, a polyvinylidene chloride, a polyacetal, a polyester, a polyester ether, a polyamide having recurring amide groups as integral parts of the main polymer chain, a polyurethane, a polycarbonate and an epoxy resin.

8. The synthetic polymer composition according to claim 1, wherein said compound (I) is selected from the group consisting of
4,4'-dihydroxy-2,2,6,6,2',2',6',6',-octamethyl-4,4'-bipiperidyyl,
4,4'-dihydroxy-1,2,2,6,6,1',2',2',6',6',-decamethyl-4,4'-bipiperidyl,
1,1'-diallyl-4,4'-dihydroxy-2,2,6,6,2',2',6',6'-octamethyl-b 4,4'-bipiperidyl,
1,1'-dibenzyl-4,4'-dihydroxy-2,2,6,6,2',2',6',6'-octamethyl-4,4'-bipiperidyl and
1,1'-bis(ethoxycarbonylmethyl)-4,4'-dihydroxy-2,2,6,6,2',2',6',6'-octamethyl-4,4'-bipiperidyl.

* * * * *